United States Patent
Keeney et al.

(10) Patent No.: US 7,888,288 B2
(45) Date of Patent: Feb. 15, 2011

(54) CONTROL OF WOODY PLANTS BY THE FOLIAR APPLICATION OF TRICLOPYR BUTOXYETHYL ESTER COMPOSITIONS FREE OF AROMATIC SOLVENTS

(75) Inventors: Franklin Nelson Keeney, Carmel, IN (US); William Newton Kline, III, Duluth, GA (US); Patrick Littleton Burch, Christiansburg, VA (US); John Lawrence Troth, Cannel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 1125 days.

(21) Appl. No.: 11/601,212

(22) Filed: Nov. 17, 2006

(65) Prior Publication Data

US 2007/0117721 A1    May 24, 2007

Related U.S. Application Data

(60) Provisional application No. 60/737,994, filed on Nov. 18, 2005.

(51) Int. Cl.
*A01N 43/40* (2006.01)

(52) U.S. Cl. .................................................. 504/254
(58) Field of Classification Search ................ 504/254
See application file for complete search history.

(56) References Cited

U.S. PATENT DOCUMENTS 5,466,659 A * 11/1995 Keeney et al. .............. 504/130

FOREIGN PATENT DOCUMENTS

WO    2006/004946    7/2007

OTHER PUBLICATIONS

Bovey et al, Honey Mesquite (Prosopis glandulosa) Control by Synergistic Action of Clopyralid: Triclopyr Mixtures, Weed Science, 1992, vol. 40, pp. 563-567.*
Dow Agrosciences LLC, Material Safety Data Sheet for Garlon 4 Herbicide.
Dow Agrosciences LLC, Specimen Label for Garlon 4 Specialty Herbicide.

* cited by examiner

*Primary Examiner*—Alton N Pryor
(74) *Attorney, Agent, or Firm*—Craig E. Mixan

(57) ABSTRACT

Triclopyr butoxyethyl ester compositions with a dearomatized aliphatic solvent or a vegetable oil ester as a carrier provide enhanced control of woody vegetation in foliar applications.

9 Claims, No Drawings

CONTROL OF WOODY PLANTS BY THE FOLIAR APPLICATION OF TRICLOPYR BUTOXYETHYL ESTER COMPOSITIONS FREE OF AROMATIC SOLVENTS

This application claims the benefit of U.S. Provisional Application Ser. No. 60/737,994 filed on Nov. 18, 2005. This invention concerns a method for controlling undesired woody vegetation by the foliar application of a triclopyr butoxyethyl ester composition with a dearomatized aliphatic solvent, vegetable oil or a vegetable oil ester as a carrier. Surprisingly, these compositions provide enhanced control of woody vegetation when compared to similar compositions containing aromatic solvents as carriers when applied to the foliage.

FIELD OF THE INVENTION

BACKGROUND OF THE INVENTION

Today's increased attention to nature and the environment has resulted in unprecedented efforts to encourage grasses, low-growing ground cover, and wildflowers on rights-of-way. Thus selective plant control treatments are desirable to remove tall-growing woody plants in vegetation control programs. Not only do such treatment programs result in effective, long lasting brush control, they leave non-target plants such as annual and perennial grasses and other desired plants to thrive because they are freed from competition for moisture, nutrients and sunlight.

One such treatment program consists of the use of basal bark or stem application of an herbicide to control undesired vegetation. This particular method is attractive because it provides not only vegetation control but also efficient placement and utilization of the herbicide composition on individual plants. U.S. Pat. No. 5,466,659 describes this method of treatment with a variety of triclopyr butoxyethyl ester compositions. In addition to this application method to apply herbicides to bark or stems of unwanted plants, it is often more efficient to apply treatments to the leaves of target vegetation, such as is done when herbicide treatments are made using ground or aerial broadcast applications or using ground directed sprays such as with a backpack sprayer or other directed spray equipment.

In order to have the herbicide penetrate into the leaves of woody plant, it is desirable to dissolve the herbicide in a non-aqueous organic carrier. As currently used, as in Garlon™ 4 herbicide, for example, such carriers for foliar applications consist of petroleum distillates such as fuel oils, e.g., diesel oil or kerosene.

However, these carriers present risks not only to the surrounding environment, but also to the applicator. In aerial applications, for example, due to applicator technique or wind conditions, over-spray onto surrounding areas may result during the application.

SUMMARY OF THE INVENTION

The present invention concerns a method for controlling undesired woody vegetation which comprises applying to the foliage of the woody vegetation an herbicidal composition comprising about 60 to about 600 grams acid equivalent/liter triclopyr butoxyethyl ester, about 25 to about 150 grams/liter emulsifier and about 200 to about 900 grams/liter of either a dearomatized aliphatic solvent, vegetable oil or an ester of a vegetable oil as a carrier, or a water dilution of the herbicidal composition. In addition to providing for a more efficient treatment procedure, i.e., foliar versus basal bark, and providing reduced exposure to aromatic carriers, the present method provides unexpected improved control of a number of key woody plants.

DETAILED DESCRIPTION OF THE INVENTION

This invention provides a method for controlling woody plants by applying to their foliage a composition comprising triclopyr butoxyethyl ester, one or more emulsifiers and a carrier of either a dearomatized aliphatic solvent, vegetable oil or an ester of a vegetable oil.

Triclopyr is the common name for 3,5,6-trichloro-2-pyridinyloxyacetic acid. This compound is a selective systemic herbicide used in the control of brush and woody vegetation, and many broad-leaved weeds, in areas such as grasslands and other uncultivated lands, industrial areas, rights-of-way, coniferous forests, oil palm, rubber plantations and rice.

The butoxyethyl ester of triclopyr is commercially available from Dow AgroSciences as Garlon™ 4 herbicide, a 4 lb acid equivalents/gallon formulation containing petroleum distillates.

Dearomatized aliphatic solvents are hydrocarbon fluids that contain minimal amounts of any aromatic components, e.g., less than one percent. The dearomatized aliphatic solvents most suitable for the present invention have a boiling point range from about 160 to about 315° C., preferably from about 200 to about 250° C. Dearomatized aliphatic solvents are available, for example, from Exxon Mobil Chemical as Exxsol™ hydrocarbon fluids. Exxsol D 80 hydrocarbon fluid is a particularly suitable dearomatized aliphatic solvent for the purposes of this invention.

Suitable vegetable oils employed in the present invention may include corn oil, soybean oil, rapeseed or canola oil, sunflower oil, linseed oil or cotton seed oil.

Suitable esters of vegetable oils employed in the present invention may include esters of corn oil, soybean oil, sunflower oil, canola oil and cotton seed oil. Preferred are those of soybean oil, sunflower oil and canola oil. Further preferred esters of vegetable oils include $C_1$-$C_4$ straight and branched chain alkyl esters of fatty acids, both saturated and unsaturated, ranging from $C_6$ to $C_{18}$. Saturated fatty acid esters include, for example, caproate, caprylate, caprate, laurate, myristate, palmitate, margarate, and stearate. Unsaturated fatty acid esters include, for example, myristoleate, palmitoleate, oleate, linoleate, and linolenate. Methyl fatty acid esters are preferred, and further, the unsaturated fatty acid esters are preferred over the saturated fatty acid esters. Preferred fatty acid esters employed in the present invention include methyl caprylate-caprate (Emery™ 2209, Henkel Corporation), methyl laurate (Emery 2296, Emery 2290, or Emery 2270, Henkel Corporation) and methyl oleate (Emery 2301, Henkel Corporation). A more preferred fatty acid ester is methyl oleate.

Suitable emulsifiers can be anionic, cationic or nonionic in character. Typical emulsifying agents include salts of alkyl sulfates, such as diethanol-ammonium lauryl sulfate; alkylarylsulfonate salts, such as calcium dodecyl-benzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkyl-naphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethyl-ammonium chloride; polyethylene glycol esters of fatty acids, such as poly-ethylene glycol stearate; block copolymers of ethylene oxide and propylene oxide; and salts of mono and dialkyl phosphate esters.

The compositions useful in the foliar applications of the present invention contain from about 60 to about 600 grams acid equivalent/liter of triclopyr butoxyethyl ester, from about 25 to about 150 grams/liter of emulsifier and from about 200 to about 900 grams/liter of carrier. Preferably the composition contains from about 60 to about 480 grams acid equivalent/liter of triclopyr butoxyethyl ester, from about 50 to about 100 grams/liter of emulsifier and from about 230 to about 865 grams/liter of carrier.

In addition to the compositions and uses set forth above, the present invention also embraces the composition and use of these triclopyr butoxyethyl ester compositions in combination with one or more additional compatible ingredients. Other additional ingredients may include, for example, one or more other herbicides, dyes, and any other additional ingredients providing functional utility, such as, for example, stabilizers, fragrants, viscosity-lowering additaments, and freeze-point depressants.

Additional herbicidal compounds employed as supplements or additaments should not be antagonistic to the activity of the triclopyr butoxyethyl ester composition as employed in the present invention. Suitable herbicidal compounds include, but are not limited to 2,4-D, 2,4-MCPA, ametryn, aminopyralid, asulam, atrazine, butafenacil, carfentrazone-ethyl, chlorflurenol, chlormequat, chlorpropham, chlorsulfuron, chlortoluron, cinosulfuron, clethodim, clopyralid, cyclosulfamuron, pyroxsulam, dicamba, dichlobenil, dichlorprop-P, diclosulam, diflufenican, diflufenzopyr, diuron, fluroxypyr, glyphosate, hexazinone, imazamox, imazapic, imazapyr, imazaquin, imazethapyr, imazosulfuron, MCPA, metsulfuron-methyl, picloram, pyrithiobac-sodium, sethoxydim, sulfometuron, sulfosate, sulfosulfuron, tebuthiuron, terbacil, thiazopyr, thifensulfuron, triasulfuron and tribenuron. Particularly useful herbicidal compounds for use with triclopyr butoxyethyl ester in foliar brush-control applications are clopyralid esters and amines, e.g., 3,6-dichloro-2-pyridinecarboxylic acid monoethanolamine salt, as well as mixtures with 2,4-D butoxyethyl ester, with fluroxypyr 1-methylheptyl ester, with picloram iso-octyl ester and with aminopyralid salts. The herbicidal composition used in the method of the present invention can be formulated with the other herbicide or herbicides, tank mixed with the other herbicide or herbicides, or applied sequentially with the other herbicide or herbicides.

Dyes may be used in the formulated composition as a marker. Generally, a preferred dye can be any oil-soluble dye selected from EPA's approved list of inerts exempt from tolerance. Such dyes, may include, for example, D&C Red #17, D&C Violet #2, and D&C Green #6. Dyes are generally added to the composition by adding the desired amount of dye to the formulated composition with agitation. Dyes are generally present in the final formulation composition in a concentration of about 0.1-1.0% by weight.

The compositions of the present invention can be applied to the foliage of the woody vegetation as is or they may be diluted with water prior to application. The diluted compositions usually applied to the woody vegetation generally contain about 0.0001 to about 20.0 weight percent triclopyr butoxyethyl ester.

The following examples illustrate the present invention.

EXAMPLES

Example 1

Preparation of Methylated Soybean Oil Formulation

Cognis 33971 emulsifier (calcium dodecylbenzene sulfonate—alkoxylated alcohol) (5.0 g) was added with stirring at room temperature to 60.45 g of technical triclopyr butoxyethyl ester and 34.55 g of Edenor ME 12-18 (methylated soybean oil). Stirring was continued until a single phase was obtained.

Example 2

Preparation of Exxsol D-80 Formulation

Sponto AC 31-2 emulsifier (mixed amine salt of dodecylbenzene sulfonate; 3.5 g) and Witconol AL 69-66 emulsifier (alcohol ethoxylate; 1.5 g) were added with stirring at room temperature to 62.1 g of technical triclopyr butoxyethyl ester and 32.9 g of Exxsol D-80 solvent (dearomatized hydrocarbon solvent). Stirring was continued until a single phase was obtained.

Example 3

Preparation of Exxsol D-80 Formulation

Witconate P-120 emulsifier (calcium salt of dodecylbenzene sulfonate; 2.88 g) and T-Det C-40 emulsifier (castor oil ethoxylate; 2.27 g) were added with stirring at room temperature to 172.1 g of technical triclopyr butoxyethyl ester, 369.1 g of technical 2,4-D butoxyethyl ester and 453.7 g of Exxsol D-80 solvent (dearomatized hydrocarbon solvent). Stirring was continued until a single phase was obtained Example 4

Herbicidal Testing

Trials were conducted at four locations in mixed and single species woody plant sites. Target woody brush was six feet or less and application was conducted over the top with hand held booms. The study was designed to compare the methylated soybean oil formulation of Example 1 and the Exxsol D-80 formulation of Example 2 to the commercially available Garlon 4 formulation that contains kerosene. The rates selected were based on the target species. In mixed brush, the rates were 1.5 and 3.0 pounds acid equivalents per acre (lbs ae/ac) (1.68 and 3.36 kilogram acid equivalent per hectare (kg ae/ha)). For Scotch broom the rates were 1.25 lbs ae/ac (1.4 kg ae/ha). The formulations were diluted in water and applied at a delivery volume of 20 gallons per acre (gpa) (187 liters per hectare (L/ha)). No surfactant was added to the mixtures. Sites were treated in the growing season and assessment of control was made the following year. The results (in percent control) are summarized in Table I.

TABLE I

Percent Control by Formulation/Rate

| Species Common Name | Methylated Soybean Oil | | Exxsol D-80 | | Kerosene Garlon 4 | |
|---|---|---|---|---|---|---|
| | 1.25 lbae/ac (1.4 kgae/ha) | | 1.25 lbae/ac (1.4 kgae/ha) | | 1.25 lbae/ac (1.4 kgae/ha) | |
| scotch broom | 90 | | 97 | | 65 | |
| | 1.5 lbae/ac (1.68 kgae/ha) | 3.0 lbae/ac (3.36 kgae/ha) | 1.5 lbae/ac (1.68 kgae/ha) | 3.0 lbae/ac (3.36 kgae/ha) | 1.5 lbae/ac (1.68 kgae/ha) | 3.0 lbae/ac (3.36 kgae/ha) |
| sweetgum | 43 | 73 | 53 | 82 | 43 | 61 |
| cherry | 30 | 50 | 33 | 47 | 30 | 37 |
| loblolly pine | 13 | 37 | 13 | 47 | 26 | 40 |
| red oak | 47 | 65 | 55 | 80 | 47 | 58 |
| water/willow oak | 47 | 62 | 40 | 78 | 47 | 62 |

A second study evaluated large aerial applications to mesquite. Alternative formulations at 0.25 lbs ae/acre (0.28 kg ae/ha) were diluted in water and were applied by fixed wing aircraft on 10 acre (4.04 hectare) plots (2 per treatment) at a delivery volume of 5 gpa (46.8 L/ha). Herbicides were applied in a mixture which consisted of triclopyr BEE and a second herbicide, Reclaim™ herbicide. No surfactant was added to the mixtures. Sites were treated in the growing season and assessment of control was made the following year. The results are summarized in Table II.

TABLE II

| Species Common Name | Percent Control by Formulation/Rate | | |
|---|---|---|---|
| | Methylated Soybean Oil | Exxsol D-80 | Kerosene Garlon 4 |
| | 0.25 lbae/ac (0.28 kgae/ha) + Reclaim™ 0.25 lbae/ac (0.28 kgae/ha) | 0.25 lbae/ac (0.28 kgae/ha) + Reclaim 0.25 lbae/ac (0.28 kgae/ha) | 0.25 lbae/ac (0.28 kgae/ha) + Reclaim 0.25 lbae/ac (0.28 kgae/ha) |
| mesquite | 68.5 | 72.9 | 42.4 |

A third study evaluated blackberry control with Crossbow™ herbicide. Alternative formulations at 0.5% v/v and 1.0% v/v were diluted in water and were applied by fixed wing aircraft on blackberry clumps (4 per treatment) as a spray to wet treatment (customary for blackberry individual plant treatment method). Surfactant was added at 0.25% v/v to the mixtures. Sites were treated in the growing season and assessment of control was made the following year. The results are summarized in Table III.

TABLE III

Percent Control by Formulation/Rate

| | Methylated Seed Oil | | Exxsol D-80 | | Crossbow kerosene | |
|---|---|---|---|---|---|---|
| Species | 0.5% | 1.0% | 0.5% | 1.0% | 0.5% | 1.0% |
| Blackberry | 98 | 100 | 80 | 100 | 91 | 90 |

What is claimed is:

1. A method for controlling undesired woody vegetation which comprises applying to the foliage of the woody vegetation an herbicidal composition comprising about 60 to about 600 grams acid equivalent/liter triclopyr butoxyethyl ester, about 50 to about 150 grams/liter emulsifier and about 200 to about 900 grams/liter of either a dearomatized aliphatic solvent, vegetable oil or an ester of a vegetable oil as a carrier, or a water dilution of the herbicidal composition.

2. The method of claim 1 in which the herbicidal composition comprises from about 60 to about 480 grams acid equivalent/liter triclopyr butoxyethyl ester, about 50 to about 100 grams/liter emulsifier and about 230 to about 865 grams/liter of either a dearomatized aliphatic solvent, vegetable oil or an ester of a vegetable oil as a carrier.

3. The method of claim 1 in which the dearomatized aliphatic solvent has a boiling point range from about 160 to about 315° C.

4. The method of claim 1 in which the dearomatized aliphatic solvent has a boiling point range from about 200 to about 250° C.

5. The method of claim 1 in which the vegetable oil is corn oil, soybean oil, sunflower oil, rapeseed or canola oil, cotton seed oil or linseed oil.

6. The method of claim 1 in which the ester of a vegetable oil is an ester of corn oil, soybean oil, sunflower oil, canola oil, or cotton seed oil.

7. The method of claim 1 in which the ester of a vegetable oil is a $C_1$-$C_4$ straight and branched chain alkyl ester of a fatty acid, both saturated and unsaturated, ranging from $C_6$ to $C_{18}$.

8. The method of claim 1 in which the ester of a vegetable oil is methyl caprylate-caprate, methyl laurate or methyl oleate.

9. The method of claim 1 in which the herbicidal composition is diluted with water prior to the application to the foliage of the woody vegetation.

* * * * *